United States Patent [19]

Ligon et al.

[11] Patent Number: 5,585,238
[45] Date of Patent: Dec. 17, 1996

[54] DETECTION OF FUNGAL PATHOGENS USING THE POLYMERASE CHAIN REACTION

[75] Inventors: James M. Ligon, Basel, Switzerland; James J. Beck, Cary, N.C.

[73] Assignee: Ciba-Geigy Corporation, Tarrytown, N.Y.

[21] Appl. No.: 233,608

[22] Filed: Apr. 25, 1994

[51] Int. Cl.$^6$ .............................. C12Q 1/68; C12P 19/34; C07H 21/04
[52] U.S. Cl. .......................... 435/6; 435/91.2; 435/91.5; 536/23.1; 536/24.2; 536/24.32; 536/24.33; 935/6; 935/8; 935/9; 935/17; 935/78
[58] Field of Search ............................ 435/6, 91.2, 91.5; 536/23.1, 24.2, 24.32, 24.33; 935/6, 8, 9, 17, 77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,324,632 | 6/1994 | Weisburg et al. | 435/6 |
| 5,447,848 | 9/1995 | Barns et al. | 435/29 |

FOREIGN PATENT DOCUMENTS

WO91/14001  9/1991  WIPO.

OTHER PUBLICATIONS

Tisserat et al., "Selective Amplification of rDNA Internal Transcribed Spacer Regions to Detect *Ophiosphaerella korrae* and *O. herpotricha*", Phytopathology, 84(5): 478–482 (1994).

Xue et al., "Pathotype identification of *Leptosphaeria maculans* with PCR and oligonucleotide primrers from ribosomal internal transribed spacer sequences", *Physiological and Molecular Plant Pathology*, 41: 179–188 (1992).

Stratogene Catalog, 1988, p. 39.

GenBank Accession No. U04237, computer printout, Jan. 4, 1994.

Johanson A., and Jeger, M. J., "Use of PCR for Detection of *Mycosphaerella fijiensis* and *M. musicola*, the Causal Agents of Sigatoka Leaf Spots in Banana and Plantain", *Mycol. Res.*, 97:670–674 (1993).

Nazar, R. N., et al, "Potential Use of PCR–amplified Ribosomal Intergenic Sequences in the Detection and Differentiation of Verticillium Wilt Pathogens", *Physiol. and Molec. Plant Pathol.*, 39:1–11 (1991).

Schlesser, K., et al., "Use of Polymerase Chain Reaction to Detect the Take–All fungus, *Gaeumannomyces graminis*, in Infected Wheat Plants", *Applied and Environ. Microbiol.*, 57(2):553–556 (1991).

White, T. J., et al., "Amplification and Direct Sequencing of Fungal Ribosomal RNA Genes for Phylogenetics", In: *PCR Protocols;* Eds.: Innes et al., al., 315–322 (1990).

Poupard, P. et al., "Molecular Characterization of *Pseudocercosporella herpotrichoides* Isolates by Amplification of Ribosomal DNA Internal Transcribed Spacers", *Plant Pathology*, 42:873–881 (1993).

*Primary Examiner*—Carla J. Myers
*Attorney, Agent, or Firm*—Andrea C. Walsh, Ph.D.; Gary M. Pace, Ph.D.

[57] ABSTRACT

DNA sequences from the Internal Transcribed Spacer of the ribosomal RNA gene region are described for different species and strains of Septoria, Pseudocercosporella and Mycosphaerella. Specific primers from within these sequences are identified as being useful for the identification of the fungal isolates using PCR-based techniques.

19 Claims, No Drawings

DETECTION OF FUNGAL PATHOGENS USING THE POLYMERASE CHAIN REACTION

FIELD OF THE INVENTION

The present invention relates to the use of species-specific primers in polymerase chain reaction assays for the detection of fungal pathogens. The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and additionally in many parts of the world to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains which are resistant to particular fungicides. As early as 1981, Fletcher and Wolfe (1981; *Proc.* 1981 *Brit. Crop Prot. Conf.*) contended that 24% of the powdery mildew populations from spring barley, and 53% from winter barley showed considerable variation in response to the fungicide triadimenol and that the distribution of these populations varied between varieties with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford; Cereal Diseases, John Wiley, 1983).

Cereal species are grown world-wide and represent a major fraction of world food production. Although yield loss is caused by many pathogens, the necrotizing pathogens Septoria and Pseudocercosporella are particularly important in the major cereal growing areas of Europe and North America (Jones and Clifford; Cereal Diseases, John Wiley, 1983). In particular, the differential symptomology caused by different isolates and species of these fungi make the accurate predictive determination of potential disease loss difficult. Consequently, the availability of improved diagnostic techniques for the rapid and accurate identification of specific pathogens will be of considerable use to field pathologists.

Four Septoria species parasitize the small grain species. *Septoria tritici* is the causative agent of leaf blotch and is virulent on wheat but also parasitizes triticale and rye. It typically causes leaf necrosis. *Septoria nodorum* is the causative agent of glume blotch and is parasitic on wheat, triticale, rye and barley and although mainly restricted to glumes is also found on leaf blades and sheaths. *Septoria avenae* is parasitic on oats, wheat and triticale and *Septoria passerinii* is restricted to barley. Septoria diseases occur in all wheat growing areas at economically important levels. Different Septoria diseases frequently occur concurrently within fields and on individual plants, where the disease symptoms may be collectively referred to as the "Septoria complex". Typically, the most commonly found species are *S. tritici* and *S. nodorum*. According to Wiese (1977; Compendium of Wheat Diseases, Amer. Phytopath. Soc: pages 42–45), the Septoria complex presently destroys nearly 2% of the world's wheat annually, the yield loss being mainly the result of impaired grain filling. Fungicide treatments can save up to 20% in cases of severe Septoria infection, but it is often difficult to distinguish between the different Septoria species at the onset of infection and this makes the decision whether or not to invest in fungicide use difficult because different cultivars display differing degrees of resistance to the various Septoria species.

The eyespot disease of cereals is caused by the fungus *Pseudocercosporella herpotrichoides* and is restricted to the basal culm of the plant. Wheat, rye, oats and other grasses are susceptible to the eyespot disease which occurs in cool, moist climates and is prevalent in Europe, North and South America, Africa and Australia. Wheat is the most susceptible cereal species, but isolates have been identified which are also virulent on other cereals. The R-strain of the fungus, for example, has also been isolated from rye and grows more slowly on wheat than the W-strain which has been isolated from wheat. Although eyespot may kill tillers or plants outright, it more usually causes lodging and/or results in a reduction in kernel size and number. Yield losses associated with eyespot are of even greater magnitude than those associated with *Septoria tritici* and *Septoria nodorum*. Typical control measures for eyespot include treatment with growth regulators to strengthen internodes, and fungicide treatment. However, the differing susceptibility of cultivars to different strains of the fungus render the predictive efficacy of fungicide treatments difficult.

Sigatoka leaf spot of banana occurs in two forms each of which is caused by a different fungus. The economically important Black Sigatoka is caused by *Mycosphaerella fijiensis*, whereas the less economically significant Yellow Sigatoka is caused by *Mycosphaerella musicola* (Johanson and Jeger, 1993; Mycol. Res. 97: 670–674). Black Sigatoka is the major problem in banana causing severe losses of 30% and more. Due to occurrence of fungicide resistance in *Mycosphaerella fijiensis*, usage of fungicide should best be limited to prevent the further occurrence of resistance. Consequently, the availability of diagnostic tools will provide an important means of identifying the appropriate circumstances in which to utilize fungicides without unnecessarily risking the development of further resistance.

Thus, there is a real need for the development of technology which will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention is drawn to methods of identification of different pathotypes of plant pathogenic fungi. The invention provides DNA sequences which show variability between different fungal pathotypes. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

This invention provides the possibility of assessing potential damage in a specific crop variety-pathogen strain relationship and of utilizing judiciously the diverse armory of fungicides which is available. Furthermore, it can be used to provide detailed information on the development and spread of specific pathogen races over extended geographical areas. The invention provides a method of detection which is especially suitable for diseases with a long latent phase such as those caused by *Septoria nodorum* or *Septoria tritici* on wheat and *Mycosphaerella fijiensis* on banana.

Kits useful in the practice of the invention are also provided. The kits find particular use in the identification of Septoria, Pseudocercosporella, and Mycosphaerella pathogens.

BRIEF DESCRIPTION OF THE SEQUENCES IN THE SEQUENCE LISTING

| | |
|---|---|
| SEQ ID NO: 1 | DNA sequence for the Internal Transcribed Spacer of *Septoria tritici.* |
| SEQ ID NO: 2 | DNA sequence for the Internal Transcribed Spacer of *Septoria nodorum.* |
| SEQ ID NO: 3 | DNA sequence for the Internal Transcribed Spacer of *Pseudocercosporella herpotrichoides* strain W (variant 1). |
| SEQ ID NO: 4 | DNA sequence for the Internal Transcribed Spacer of *Pseudocercosporella herpotrichoides* strain R. |
| SEQ ID NO: 5 | DNA sequence for the Internal Transcribed Spacer of *Mycosphaerella fijiensis.* |
| SEQ ID NO: 6 | DNA sequence for the Internal Transcribed Spacer of *Mycosphaerella musicola.* |
| SEQ ID NO: 7 | Oligonucleotide Primer JB433 |
| SEQ ID NO: 8 | Oligonucleotide Primer JB434 |
| SEQ ID NO: 9 | Oligonucleotide Primer JB525 |
| SEQ ID NO: 10 | Oligonucleotide Primer JB527 |
| SEQ ID NO: 11 | Oligonucleotide Primer JB445 |
| SEQ ID NO: 12 | Oligonucleotide Primer JB446 |
| SEQ ID NO: 13 | Oligonucleotide Primer JB526 |
| SEQ ID NO: 14 | Oligonucleotide Primer JB536 |
| SEQ ID NO: 15 | Oligonucleotide Primer JB537 |
| SEQ ID NO: 16 | Oligonucleotide Primer JB538 |
| SEQ ID NO: 17 | Oligonucleotide Primer JB539 |

-continued

| | |
|---|---|
| SEQ ID NO: 18 | Oligonucleotide Primer JB540 |
| SEQ ID NO: 19 | Oligonucleotide Primer JB541 |
| SEQ ID NO: 20 | Oligonucleotide Primer JB542 |
| SEQ ID NO: 21 | Oligonucleotide Primer JB543 |
| SEQ ID NO: 22 | Oligonucleotide Primer JB544 |
| SEQ ID NO: 23 | Oligonucleotide Primer JB547 |
| SEQ ID NO: 24 | Oligonucleotide Primer JB548 |
| SEQ ID NO: 25 | Oligonucleotide Primer JB442 |
| SEQ ID NO: 26 | Oligonucleotide Primer JB443 |
| SEQ ID NO: 27 | Oligonucleotide Primer JB545 |
| SEQ ID NO: 28 | Oligonucleotide Primer JB546 |
| SEQ ID NO: 29 | Oligonucleotide Primer JB549 |
| SEQ ID NO: 30 | Oligonucleotide Primer JB444 |
| SEQ ID NO: 31 | Oligonucleotide Primer JB451 |
| SEQ ID NO: 32 | Oligonucleotide Primer JB440 |
| SEQ ID NO: 33 | Oligonucleotide Primer JB449 |
| SEQ ID NO: 34 | Oligonucleotide Primer JB448 |
| SEQ ID NO: 35 | Oligonucleotide Primer JB441 |
| SEQ ID NO: 36 | Oligonucleotide Primer JB450 |
| SEQ ID NO: 37 | Oligonucleotide Primer JB452 |
| SEQ ID NO: 38 | Oligonucleotide Primer ITS1 |
| SEQ ID NO: 39 | Oligonucleotide Primer ITS2 |
| SEQ ID NO: 40 | Oligonucleotide Primer ITS3 |
| SEQ ID NO: 41 | Oligonucleotide Primer ITS4 |
| SEQ ID NO: 42 | Oligonucleotide Primer OPB-12 |
| SEQ ID NO: 43 | Oligonucleotide Primer OPE-6 |
| SEQ ID NO: 44 | Oligonucleotide Primer OPE-12 |
| SEQ ID NO: 45 | Oligonucleotide Primer OPB-19 |
| SEQ ID NO: 46 | Oligonucleotide Primer OPE-15 |
| SEQ ID NO: 47 | DNA sequence for the Internal Transcribed Spacer of *Pseudocercosporella herpotrichoides* strain W (variant 2). |

DETAILED DESCRIPTION OF THE INVENTION

The present invention provides unique DNA sequences which are useful in identifying different pathotypes of plant pathogenic fungi. Particularly the DNA sequences can be used as primers in PCR based analysis for the identification of fungal pathotypes. The DNA sequences of the invention include the Internal Transcribed Spacer (ITS) of the ribosomal RNA gene regions of particular fungal pathogens as well as primers which are derived from these regions which are capable of identifying the particular pathogen. These ITS DNA sequences from different pathotypes within a pathogen species or genus which vary between the different members of the species or genus can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol.* 57: 553–556) and random amplified polymorphic DNA (i.e. RAPD) markers were able to distinguish numerous races of *Gremmeniella abietina,* the causal agent of scleroderris canker in conifers.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units each of which encodes three mature subunits of 18S, 5.8S, and 28S respectively. These subunits are separated by two internal transcribed spacers, ITS1 and ITS2, of around 300 bp (White et al., 1990; In: PCR Protocols; Eds.: Innes et al.; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer (ITS) of the ribosomal RNA gene region of different plant pathogens. The ITS DNA sequences from different pathotypes within a pathogen species or genus vary between the different members of the species or genus. Once having determined the ITS sequences of a pathogen, these sequences can be aligned with other ITS sequences. In this manner, primers can be derived from the ITS sequences. That is, primers can be designed based on regions within the ITS regions that contain the greatest differences in sequence among the fungal pathotypes. These sequences and primers based on these sequences can be used to identify specific pathogen members.

Particular DNA sequences of interest include ITS DNA sequences from Septoria, particularly, *Septoria nodorum* and *Septoria tritici;* Mycosphaerella, particularly *Mycosphaerella fijiensis* and *Mycosphaerella musicola;* Pseudocercosphorella, particularly *Pseudocercosporella herpotrichoides,* more particularly for the W-strain and the R-strain of *Pseudocercosporella herpotrichoides.* Such ITS DNA sequences as well as primers of interest are given in SEQ ID NO: 1-47. The sequences find use in the PCR-based identification of the pathotypes of interest.

Methods for the use of the primer sequences of the invention in PCR analysis are well known in the art. For example, see U.S. Pat. Nos. 4,683,195 and 4,683,202 as well as Schlesser et al. (1991) *Applied and Environ. Microbiol.* 57:553–556. See also, Nazar et al. (1991; *Physiol. and Molec. Plant Pathol.* 39: 1–11) which used PCR amplification to exploit differences in the ITS regions of *Verticillium albo-atrum* and *Verticillium dahliae* and therefore distinguish between the two species; and Johanson and Jeger (1993; *Mycol. Res.* 97: 670–674) who used similar techniques to distinguish the banana pathogens *Mycosphaerella fijiensis* and *Mycospharella musicola.*

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications,* Innes et al. (Eds.); pages 282–287.

Alternatively, the ITS regions of interest can be determined by PCR amplification. Primers to amplify the entire ITS region were designed according to White et al. (1990; In: PCR Protocols; Eds.: Innes et al. pages 315–322) and the amplified ITS sequence was subcloned into the pCRII cloning vector. The subcloned sequence included the lefthand ITS (ITS1), the righthand ITS (ITS2) as well as the centrally located 5.8S rRNA gene. This was undertaken for *Septoria nodorum* and *Septoria tritici,* numerous Pseudocercosporella isolates and *Mycosphaerella fijiensis* and *Mycosphaerella musicola.*

The ITS sequences were determined and within each pathogen group the sequences were compared to locate divergences which might be useful to test in PCR to distinguish the different species and/or strains. The sequences of the ITS regions which were determined are shown as Sequence ID's 1 to 6 and 47. From the identification of divergences numerous primers were synthesized and tested in PCR-amplification. Templates used for PCR-amplification testing were firstly purified pathogen DNA, and subsequently DNA isolated from infected host plant tissue. Thus it was possible to identify pairs of primers which were diagnostic i.e. which identified one particular pathogen species or strain but not another species or strain of the same pathogen. Preferred primer combinations are able to distinguish between the different species or strains in infected host tissue i.e. host tissue which has previously been infected with a specific pathogen species or strain.

This invention provides numerous primer combinations which fulfill this criterion for different Septoria and Mycosphaerella species and different strains of Pseudocercosporella. The primers of the invention are designed based on sequence differences among the fungal ITS regions. A minimum of one base pair difference between sequences can permit design of a discriminatory primer. Primers designed to a specific fungal DNA's ITS region can be used in combination with a primer made to a conserved sequence region within the ribosomal DNA's coding region to amplify species-specific PCR fragments. In general, primers should have a theoretical melting temperature between about 60 to about 70 degree C. to achieve good sensitivity and should be void of significant secondary structure and 3' overlaps between primer combinations. Primers are generally at least about 5 to about 10 nucleotide bases.

The usefulness of cloned ITS sequences for the selection of primers for diagnostic purposes is largely due to their rapid evolutionary divergence. For example, W-type and R-type isolates of the pathogen *Pseudocercosporella herpotrichoides* were found to have divergent ITS sequences from which diagnostic primers were developed. However, the rapid divergence within the ITS sequence is apparent from the observation that two different sequence variants of the W-type were identified. The sequence identity within the W-type was 99.4%, whereas that between W and R-types was 98.6% suggesting a closer evolutionary relationship between the two W variants than was found between the W and the R-types. This closer relationship is also apparent from their similar host pathogenicity of the two isolates with divergent ITS sequences.

In addition to developing primers from ITS-derived sequences for PCR diagnosis of fungal isolates, the invention also encompasses the identification of primers from RAPD primer libraries which can distinguish between *Septoria nodorum* and *Septoria tritici* when used in PCR. The primers screened are commercially available and were obtained from Operon Technologies Incorporated (Alameda, Calif.). Screening on Septoria genomic DNA identified two primers which were able to detect only *S. tritici* and three which were able to detect only *S. nodorum*.

The present invention lends itself readily to the preparation of "kits" containing the elements necessary to carry out the process. Such a kit may comprise a carrier being compartmentalized to receive in close confinement therein one or more container means, such as tubes or vials. One of said container means may contain unlabeled or detectably labeled DNA primers. The labeled DNA primers may be present in lyophilized form, or in an appropriate buffer as necessary. One or more container means may contain one or more enzymes or reagents to be utilized in PCR reactions. These enzymes may be present by themselves or in admixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show, without limitation, typical experimental protocols which can be used in the isolation of ITS sequences, the selection of suitable primer sequences, the testing of primers for selective and diagnostic efficacy, and the use of such primers for disease and fungal isolate detection. Such examples are provided by way of illustration and not by way of limitation.

EXAMPLES

Example 1

Fungal Isolates and Genomic DNA Extraction

Viable fungal isolates of *S. nodorum, S. tritici, S. passerini, S. glycines, Pseudocercosporella herpotrichoides, Pseudocercosporella aestiva, Mycosphaerella citri, Mycosphaerella graminicola, Mycosphaerella fijiensis* and *Mycosphaerella musicola* were obtained from the American Type Culture Collection. Fungi were grown in 150 ml potato dextrose broth inoculated with mycelial fragments from PDA (Potato Dextrose Agar) cultures. Cultures were incubated on an orbital shaker at 28° C. for 7–11 days. Mycelia were pelleted by centrifugation and then ground in liquid nitrogen and total genomic DNA extracted using the protocol of Lee and Taylor (1990; In: *PCR Protocols: A Guide to Methods and Applications;* Eds.: Innes et al.; pages 282–287).

Dr. Bruce McDonald from Texas A&M University supplied genomic DNA from ten isolates of *S. nodorum* and nine isolates of *S. tritici.* Dr Chris Caten of Birmingham University provided six isolates of *Septoria nodorum* purified fungal DNA. Purified genomic DNA from 12 isolates of *Pseudocercosporella herpotrichoides* was obtained from Dr. Paul Nicholson of the John Innes Centre, Norwich, UK. Six of these isolates are of the W-type; the other six isolates are of the R-type. These isolates were typed based on pathogenicity and RFLP studies. Andrea Johanson of the Natural Resources Institute supplied genomic DNA of six isolates of *M. musicola,* six isolates of *M. fijiensis* and a single isolate of *Mycosphaerella musae.*

TABLE 1

Source of Test Isolates

| Isolate | Species | Origin | Source |
|---|---|---|---|
| ATCC# 24425 | *S. nodorum* | Montana | ATCC[1] |
| XA1.1 | *S. nodorum* | Texas | B. McDonald[2] |
| Xa5A.2 | *S. nodorum* | Texas | B. McDonald |
| YA3.1 | *S. nodorum* | Texas | B. McDonald |
| XD2.1 | *S. nodorum* | Texas | B. McDonald |
| YB2.2 | *S. nodorum* | Texas | B. McDonald |
| 93HBh6a | *S. nodorum* | Oregon | B. McDonald |
| 93A3a | *S. nodorum* | Oregon | B. McDonald |
| 93AYa | *S. nodorum* | Oregon | B. McDonald |
| 93HBh8a | *S. nodorum* | Oregon | B. McDonald |
| 93C5a | *S. nodorum* | Oregon | B. McDonald |
| ATCC# 26517 | *S. tritici* | Minnesota | ATCC |
| BS3 | *S. nodorum* | Ireland | C. Caten[3] |
| BS6 | *S. nodorum* | Ireland | C. Caten |
| BS175 | *S. nodorum* | England | C. Caten |
| BS425 | *S. nodorum* | England | C. Caten |
| alpha'5 | *S. nodorum* | France | C. Caten |
| m300 | *S. nodorum* | England | C. Caten |
| TKV2a | *S. tritici* | Turkey | B. McDonald |
| SYK2 | *S. tritici* | Syria | B. McDonald |
| ISZC36.2 | *S. tritici* | Israel | B. McDonald |
| CNRC4a.1 | *S. tritici* | Canada | B. McDonald |
| ALA1a | *S. tritici* | Algeria | B. McDonald |
| ETK1 | *S. tritici* | Ethiopia | B. McDonald |
| GEB2a.1 | *S. tritici* | Germany | B. McDonald |
| UK92D2 | *S. tritici* | United Kingdom | B. McDonald |
| DNB1a | *S. tritici* | Denmark | B. McDonald |
| ATCC# 38699 | *S. glycines* | Illinois | ATCC |
| ATCC# 22585 | *S. passerini* | Minnesota | ATCC |
| ATCC# 42040 | *P. herpotrichoides*-wheat | | ATCC |
| ATCC# 62012 | *P. aestiva* | Germany | ATCC |
| ATCC# 60972 | *P. herp.* var. herp.-barley | Germany | ATCC |
| W1 | *P. herpotrichoides* | United Kingdom | P. Nicholson[4] |
| W2 | *P. herpotrichoides* | United Kingdom | P. Nicholson |
| W3 | *P. herpotrichoides* | United Kingdom | P. Nicholson |
| W4 | *P. herpotrichoides* | United Kingdom | P. Nicholson |
| W5 | *P. herpotrichoides* | New Zealand | P. Nicholson |
| W6 | *P. herpotrichoides* | Italy | P. Nicholson |
| R1 | *P. herpotrichoides* | Belgium | P. Nicholson |
| R2 | *P. herpotrichoides* | New Zealand | P. Nicholson |
| R3 | *P. herpotrichoides* | Germany | P. Nicholson |
| R4 | *P. herpotrichoides* | Sweden | P. Nicholson |
| R5 | *P. herpotrichoides* | United Kingdom | P. Nicholson |
| R6 | *P. herpotrichoides* | United Kingdom | P. Nicholson |
| ATCC# 22116 | *M. fijiensis* | Philippines | ATCC |
| ATCC# 22115 | *M. musicola* | Philippines | ATCC |
| ATCC# 24046 | *M. citri* | Florida | ATCC |
| ATCC# 62714 | *M. graminicola* | Montana | ATCC |
| PA92 | *M. fijiensis* | Panama | A. Johanson[5] |
| PNG291 | *M. fijiensis* | Papua New Guinea | A. Johanson |
| GH6-3 | *M. fijiensis* | Ghana | A. Johanson |

TABLE 1-continued

Source of Test Isolates

| Isolate | Species | Origin | Source |
|---|---|---|---|
| TG120 | M. fijiensis | Tonga | A. Johanson |
| HSB4 | M. fijiensis | Honduras | A. Johanson |
| RT689 | M. fijiensis | Rarotonga (Cook Is.) | A. Johanson |
| CR548 | M. musicola | Costa Rica | A. Johanson |
| CM61 | M. musicola | Cameroon | A. Johanson |
| CU823 | M. musicola | Cuba | A. Johanson |
| MQ103 | M. musicola | Martinique | A. Johanson |
| CI31 | M. musicola | Ivory Coast | A. Johanson |
| CB90 | M. musicola | Colombia | A. Johanson |
| BD1-4 | M. musae | Barbados | A. Johanson |

[1]American Type Culture Collection, Rockville, Maryland USA
[2]Dr. Bruce McDonald, Texas A & M University, USA
[3]Dr. Chris Caten, Birmingham University, UK
[4]Dr. Paul Nicholson, John Innes Center, UK
[5]Dr Andrea Johanson, Natural Resources Institute, UK

Example 2

Isolation of the Internal Transcribed Spacer (ITS) Regions

The approximately 550 bp internal transcribed spacer region fragments were PCR amplified from 25 ng of genomic DNA isolated from S. nodorum (ATCC#24425), S. tritici (ATCC#26517), Pseudocercosporella herpotrichoides isolates R1, R2, W2 and W5, M. fijiensis (ATCC#22115) and M. musicola (ATCC#22115) using 50 pmol of primers ITS1 (5'-TCCGTAGGTGAACCTGCGG-3'; SEQ ID NO: 38) and ITS4 (5'-TCCTCCGCTTATTGATATGC-3'; SEQ ID NO:41). PCRs were performed as described in EXAMPLE 4 except that reactions were done in 100 μl and annealing was done at of 50° C. The ITS fragments were purified by isopropanol precipitation according to Maniatis et al. (1982; *Molecular Cloning;* Eds.: Maniatis et al.; pages 461–462). The DNA was resuspended in 50 μl $dH_2O$ and cloned using the Invitrogen Corporation's (San Diego, Calif.) TA Cloning Kit (part no. K2000-01) using the pCRII cloning vector. The DNA sequences of the ITS regions were determined by the dideoxy method using the Applied Biosystems (Foster City, Calif.) automated sequencer model 373A with the primers ITS1 (see sequence above), ITS2 (5'-GCTGCGTTCTTCATCGATGC-3'; SEQ ID NO:39), ITS4 (see sequence above) and the M13 universal-20 (5'-GTAAAACGACGGCCAGT-3'; SEQ ID NO:48) and Reverse (5'-AACAGCTATGACCATG-3'; SEQ ID NO:49) primers. The ITS primers ITS1, ITS2, ITS3, and ITS4 used for cloning the ITS regions are detailed in White et al. (1990; In: PCR Protocols; Eds.: Innes et al. pages 315–322).

Example 3

DNA Extraction from Wheat and Banana Leaves

DNA was extracted from wheat leaves using a modified version of the Rapid DNA Extraction protocol from the MicroProbe Corporation's (Garden Grove, Calif.) IsoQuick Nucleic Acid Extraction Kit (cat# MXT-020-100). Typical yields were 5–10 μg of total DNA from 0.2 g of leaf tissue. Approximately 100 ng of total DNA were used in each PCR assay.

Modified Rapid DNA Extraction

Before using kit for the first time, the entire contents of Reagent 2A (20×Dye Concentrate) were added to Reagent 2 (Extraction Matrix).

(1) Approximately 0.2 g of leaf sample were added to a 1.5 ml eppendorf tube containing 50 μl sample buffer A and 50•1 #1 lysis solution. The leaf sample was ground with a Kontes pestle.

(2) Reagent 2 (Extraction Matrix) was shaken vigorously. 350•1 of reagent 2 were added to the sample lysate.

(3) 200 μl of Reagent 3 were added (Extraction Buffer) to the sample. The sample was vortexed 20 sec.

(4) Microcentrifugation at 12,000×g for 5 min.

(5) The aqueous phase (upper layer) was transferred to a new microcentrifuge tube. This volume was typically about 200 μl.

(6) 0.1×the volume of the aqueous phase of Reagent 4 (Sodium Acetate) to the aqueous phase sample.

(7) An equal volume of isopropanol was added to the aqueous phase sample followed by vortexing.

(8) Microcentrifugation at 12,000×g for 10 min.

(9) The supernatant was discarded without disturbing the nucleic acid pellet. 0.5 ml of –20° C. 70% ethanol was added to the pellet. The tube was vortexed to mix.

(10) Microcentrifugation at 12,000×g for 5 min.

(11) The supernatant was discarded and the pellet was allowed to dry.

(12) The nucleic acid pellet was dissolved in 50 μl Reagent 5 (RNase-free water).

Example 4

Polymerase Chain Reaction Amplification

Polymerase chain reactions were performed with the GeneAmp Kit from Perkin-Elmer/Cetus (Norwalk, Conn.; part no. N808-0009) using 50 mM KCl, 2.5 mM $MgCl_2$, 10 mM Tris-HCl, pH 8.3, containing 100 μM of each TTP, dATP, dCTP, and dGTP, 50 pM primer, 2.5 units of Taq polymerase and 25 ng of genomic DNA in a final volume of 50 μl. Reactions were run for 30 cycles of 15 s at 94° C., 15 s at 50° C., 60° C. or 70° C., and 45 s at 72° C. in a Perkin-Elmer/Cetus Model 9600 thermal cycler. The products were analyzed by loading 20 μl of each PCR sample on a 1.1–1.2% agarose gel and electrophoresed.

Example 5

Synthesis and Purification of Oligonucleotides

Oligonucleotides (primers) were synthesized on an Applied Biosystems 380A DNA synthesizer using B-cyanothyl-phosphoramidite chemistry.

Example 6

Selection of Species-specific Primers

The ITS sequences of *S. nodorum, S. tritici, P. herpotrichoides* strains R and W, *M. fijiensis* and *M. musicola* were aligned. Sets of primers were synthesized according to EXAMPLE 5 based on analysis of the aligned sequences. Primers were designed to the regions that contained the greatest differences in sequence among the fungal species. In addition, the published ribosomal gene-specific primers ITS1, ITS2, ITS3 and ITS4 (White et al., 1990; In: PCR Protocols; Eds.: Innes et al. pages 315–322) were synthesized for testing in combination with the primers specific for the ITS region.

of *S. nodorum, S. tritici, M. fijiensis* and *M. musicola*. The PCR conditions were essentially the same as described in EXAMPLE 4 except the number of PCR cycles was increased to 35, the annealing temperature was 30° C. and only 5 picamoles of each primer were used. Five RAPD primers were identified that differentiate purified genomic DNA of *S. nodorum, S. tritici, M. fijiensis* and *M. musicola*. Primers OPB-12 and OPE-6 produced a single fragment

TABLE 2

Primer Design for Fungal Detection

| Primer Template | Primer Name | Primer Sequence |
|---|---|---|
| S. nodorum | JB433 | 5' ACACTCAGTAGTTTACTACT 3' (SEQ ID NO: 7) |
| S. nodorum | JB434 | 5' TGTGCTGCGCTTCAATA 3' (SEQ ID NO: 8) |
| S. nodorum | JB525 | 5' GCGACTTGTGCTGCGCTTCAATA 3' (SEQ ID NO: 9) |
| S. nodorum | JB527 | 5' CATTACACTCAGTAGTTTACTACT 3' (SEQ ID NO: 10) |
| S. tritici | JB445 | 5' CTGCGTCGGAGTTTACG 3' (SEQ ID NO: 11) |
| S. tritici | JB446 | 5' CGAGGCTGGAGTGGTGT 3' (SEQ ID NO: 12) |
| S. tritici | JB526 | 5' CCCAGCGAGGCTGGAGTGGTGT 3' (SEQ ID NO: 13) |
| P. herp. | JB536 | 5' CTGGGGGCTACCCTACTTGGTAG 3' (SEQ ID NO: 14) |
| P. herp. | JB537 | 5' GGGGGCTACCCTACTTGGTAG 3' (SEQ ID NO: 15) |
| P. herp. | JB538 | 5' ACTTGGTAGGGTTTAGAGTCGTCA 3' (SEQ ID NO: 16) |
| P. herp. | JB539 | 5' CTTCGGTAAGGTTTAGAGTCGTCG 3' (SEQ ID NO: 17) |
| P. herp. | JB540 | 5' GGGGGCCACCCTACTTCGGTAA 3' (SEQ ID NO: 18) |
| P. herp. | JB541 | 5' CCACTGATTTTAGAGGCCGCGAG 3' (SEQ ID NO: 19) |
| P. herp. | JB542 | 5' CCACTGATTTTAGAGGCCGCGAA 3' (SEQ ID NO: 20) |
| P. herp. | JB543 | 5' CCTGTAAAAAATTGGGGGTTA 3' (SEQ ID NO: 21) |
| P. herp. | JB544 | 5' CCTGTAAAAAATTGGGGGTTG 3' (SEQ ID NO: 22) |
| M. fijiensis | JB547 | 5' ATTACCGAGTGAGGGCTCACGC 3' (SEQ ID NO: 23) |
| M. fijiensis | JB548 | 5' GTTGCTTCGGGGGCGACCTG 3' (SEQ ID NO: 24) |
| M. fijiensis | JB442 | 5' TCGGGGGCGACCTGCCG 3' (SEQ ID NO: 25) |
| M. fijiensis | JB443 | 5' CCGGAGGCCGTCTA 3' (SEQ ID NO: 26) |
| M. fijiensis | JB545 | 5' CCACAACGCTTAGAGACGGACAG 3' (SEQ ID NO: 27) |
| M. fijiensis | JB546 | 5' CACCCGCACTCCGAAGCGAATT 3' (SEQ ID NO: 28) |
| M. fijiensis | JB549 | 5' GATCCGAGGTCAACCTTTGAATAA 3' (SEQ ID NO: 29) |
| M. fijiensis | JB444 | 5' GGTCAACCTTTGAATAA 3' (SEQ ID NO: 30) |
| M. musicola | JB451 | 5' CCTTTGTGAACCACACCT 3' (SEQ ID NO: 31) |
| M. musicola | JB440 | 5' CTGCCGGCGAACTT 3' (SEQ ID NO: 32) |
| M. musicola | JB449 | 5' ACCCTGCCGGCGAACTT 3' (SEQ ID NO: 33) |
| M. musicola | JB448 | 5' GCGACCCTGCCGGCGAAC 3' (SEQ ID NO: 34) |
| M. musicola | JB441 | 5' TAGCCGGGAGACTTTGG 3' (SEQ ID NO: 35) |
| M. musicola | JB450 | 5' TCTGCGTCGGAGTTCC 3' (SEQ ID NO: 36) |
| M. musicola | JB452 | 5' CCGCGCTCCGGAGCGAAC 3' (SEQ ID NO: 37) |
| 18S rDNA | ITS1 | 5' TCCGTAGGTGAACCTGCGG 3' (SEQ ID NO: 38) |
| 5.8S rDNA | ITS2 | 5' GCTGCGTTCTTCATCGATGC 3' (SEQ ID NO: 39) |
| 5.8S rDNA | ITS3 | 5' GCATCGATGAAGAACGCAGC 3' (SEQ ID NO: 40) |
| 25S rDNA | ITS4 | 5' TCCTCCGCTTATTGATATGC 3' (SEQ ID NO: 41) |

Example 7

Selection of Random Amplified Polymorphic DNA (RAPD) Primers

Two RAPD primer libraries (kits B and E) of twenty oligonucleotides each were purchased from Operon Technologies Incorporated (Alameda, Calif.). The primers were tested for their ability to differentiate purified genomic DNA when amplified with *S. tritici* genomic DNA. Primers OPE-12, OPB-19 and OPE-15 produced single fragments from *S. nodorum* genomic DNA. Primers OPB-12 and OPE-6 did not produce any amplification products from *S. nodorum M. fijiensis* and *M. musicola* genomic DNA. Primers OPE-12, OPB-19 and OPE-15 did not amplify any fragments from genomic *S. tritici, M. fijiensis* or *M. musicola* DNA.

TABLE 3

RAPD Primers for Septoria Diagnosis

| Source of template DNA | Primer | Sequence of primer | Approximate size of amplified fragment |
|---|---|---|---|
| S. tritici | OPB-12 | 5'-CCTTGACGCA-3' (SEQ ID NO: 42) | 1.3 kb |
| S. tritici | OPE-6 | 5'-AAGACCCCTC-3' (SEQ ID NO: 43) | 1.0 kb |
| S. nodorum | OPE-12 | 5'-TTATCGCCCC-3' (SEQ ID NO: 44) | 2.2 kb |
| S. nodorum | OPB-19 | 5'-ACCCCCGAAG-3' (SEQ ID NO: 45) | 1.1 kb |
| S. nodorum | OPE-15 | 5'-ACGCACAACC-3' (SEQ ID NO: 46) | 1.3 kb |

Example 8

Determination of Primer Specificity to Purified Fungal Genomic DNA

PCRs were performed according to EXAMPLE 4 using different primer combinations in an attempt to amplify a single species-specific fragment. Species-specific PCR amplification products were produced from primers designed from the ITS region between the 18S and 25S ribosomal DNA subunits of each fungal strain of interest.

TABLE 4

| | ITS-derived diagnostic PCR primers | | |
|---|---|---|---|
| Source of template DNA | 5'Primer | 3'Primer | Approximate size of amplified fragment |
| Septoria nodorum | JB433 | JB434 | 448 bp |
| | JB433 | ITS4 (JB415) | 553 bp |
| | ITS1 (JB410) | JB434 | 478 bp |
| | ITS3 (JB414) | JB434 | 232 bp* |
| | JB527 | JB525 | 458 bp |
| Septoria tritici | JB445 | ITS4 (JB415) | 407 bp |
| | ITS1 (JB410) | JB446 | 345 bp |
| | ITS3 (JB414) | JB446 | 143 bp* |
| | JB445 | JB446 | 204 bp* |
| M. fijiensis | JB443 | ITS4 (JB415) | 418 bp |
| | ITS1 (JB410) | JB444 | 482 bp |
| | JB443 | JB444 | 366 bp* |
| | ITS3 (JB414) | JB444 | 281 bp* |
| | ITS1 (JB410) | JB549 | 489 bp |
| M. musicola | JB449 | ITS4 (JB415) | 430 bp |
| | JB448 | ITS4 (JB415) | 449 bp* |
| | JB448 | ITS2 (JB411) | 138 bp* |
| | JB450 | ITS4 (JB415) | 390 bp* |
| P. herpotrichoides | JB536 | JB541 | 415 bp+ |
| | JB536 | JB543 | 502 bp+ |
| | JB537 | JB541 | 413 bp+ |
| | JB537 | JB543 | 500 bp+ |
| | JB538 | JB541 | 401 bp+ |
| | JB538 | JB543 | 488 bp+ |
| | JB536 | ITS4 (JB415) | 560 bp+ |
| | JB537 | ITS4 (JB415) | 558 bp+ |
| | JB538 | ITS4 (JB415) | 546 bp+ |
| | ITS1 (JB410) | JB541 | 482 bp+ |
| | ITS1 (JB410) | JB543 | 569 bp+ |
| | ITS1 (JB410) | JB542 | 482 bp+ |
| | ITS1 (JB410) | JB544 | 569 bp++ |
| | JB540 | ITS4 (JB415) | 558 bp++ |
| | JB539 | ITS4 (JB415) | 545 bp++ |
| | JB540 | JB542 | 413 bp++ |
| | JB540 | JB544 | 500 bp++ |
| | JB539 | JB542 | 400 bp++ |
| | JB539 | JB544 | 487 bp++ |

*Primer combination amplified some fragments by false priming but none were the size of the desired fragment.
+ Primers amplified the correct size fragment from both R-type and W-type of Pseudocercosporella herpotrichoides.
++ Primer combination amplified the correct size fragment from the R-type of P. herpotrichoides only.

Example 9

Determination of Primer Specificity to Plant Tissue Infected with Fungi

Total genomic DNA was isolated from healthy wheat leaves, wheat leaves infected with S. nodorum, wheat leaves infected with S. tritici and wheat leaves infected with both S. nodorum and S. tritici using the protocol described in EXAMPLE 3. PCRs were performed as described in EXAMPLE 4 testing the primer combinations listed in EXAMPLE 8 against DNA from the wheat leaves.

The S. tritici-specific primer JB446 and ITS1(JB410) amplified a 345 bp fragment from purified S. tritici DNA, from S. tritici-infected wheat leaf tissue and from a wheat leaf sample infected with both S. tritici and S. nodorum. The primer set did not amplify a diagnostic fragment from healthy wheat leaf tissue nor from S. nodorum-infected wheat tissue. Similarly, the S. tritici-specific primers JB445 and ITS4(JB415) amplified a 407 bp fragment from the same tissues as the primer combination JB446 and ITS1(JB410) and was also diagnostic.

Similarly diagnostic results were obtained with the S. nodorum-specific primers JB433 and JB434. The primers amplified a 448 bp fragment from S. nodorum-infected wheat tissue, from a wheat leaf sample infested with both S. nodorum and S. tritici, as well as from purified genomic DNA of S. nodorum. The primer combination JB433 and JB434 did not amplify any fragments from healthy wheat tissue, from S. tritici-infected wheat tissue or from purified genomic DNA of S. tritici. The S. nodorum-specific primers JB527 and JB525 amplified a 458 bp fragment from the same genomic DNAs and wheat tissues as the JB433 and JB434 combination.

Total genomic DNA was also isolated from healthy banana leaves and from banana leaves infected with M. fijiensis using the protocol described in EXAMPLE 3. PCRs were performed as described in EXAMPLE 4 testing the M. fijiensis primer combinations listed in EXAMPLE 8 against DNA from the banana leaves.

The M. fijiensis-specific primer JB549 and ITS1(JB410) amplified a 489 bp fragment from purified M. fijiensis DNA and from M. fijiensis-infected banana leaf tissue. The primer set did not amplify a diagnostic fragment from healthy banana leaf tissue. The M. fijiensis-specific primer combinations JB443/ITS4(JB415) and ITS1(JB410)/JB444 amplified a 418 bp fragment and a 482 bp fragment, respectively, from the same genomic DNA and banana leaf tissue as the JB549 and ITS1(JB410) primer combination.

Example 10

Determination of Cross-reactivity of Species-specific Primers with Other Species and Isolates Purified fungal genomic DNAs were obtained as described in EXAMPLE 1 and PCR assayed as described in EXAMPLE 4 using the species-specific primers. Other fungal DNA species and isolates were tested for the species-specific primers ability to cross-react with them.

The S. tritici-specific primer JB446 and ITS1(JB410) amplified a 345 bp fragment from all of the S. tritici isolates listed in EXAMPLE 1. There was no cross-reactivity with purified genomic DNA of S. nodorum, S. glycines or S. passerini. None of these other fungal species produced an amplification product with the S. tritici-specific primers.

A 448 bp fragment was amplified from all of the S. nodorum isolates listed in EXAMPLE 1 using the S. nodorum-specific primers JB433 and JB434. Similarly the S. nodorum-specific primers JB527 and JB525 amplified a 458 bp fragment from all the S. nosorum isolates listed in EXAMPLE 1. *S. tritici, S. glycines* and *S. passerini* did not produce any amplification products when assayed with the either of the *S. nodorum*-specific primer sets JB433 and JB434 or JB527 and JB525.

Previously, the different Septoria species were identifiable by examination under the microscope, and the identification of the different Pseudocercosporella strains has been possible only by pathological tests. Similarly, the unambiguous identification of *Mycosphaerella musicola* and *Mycosphaerella fijiensis* has been difficult, and even the isolation of mature perithecia does not always allow accurate identification (Pons, 1990; In: Sigatoka Leaf Spot Diseases of Banana, Eds. RA Fullerton and RH Stover, International Network for the Improvement of Banana and Plantain, France). Currently immunodiagnostic kits utilizing ELISA technology are routinely used to identify *Septoria tritici, Septoria nodorum, Pseudocercosporella herpotrichoides* and other pathogen, but this technology lacks the accuracy, detection limit and ability to distinguish different isolates of the instant invention. In consequence, the development of a DNA test for the rapid identification of different strains of these fungi offers real advantages not only to fungal taxonomists, but also for disease management and selective fungicide use in the field.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

Deposits

The following deposits were made on Mar. 28, 1994, at Agricultural Research Service, Patent Culture Collection (NRRL), Northern Regional Research Center, 1815 North University Street, Peoria, Ill. 61604, U.S.A.:

| | |
|---|---|
| 1. HB101 DH5d (pCRW2-1; SEQ ID NO: 3) | Accession No. NRRL B-21231 |
| 2. HB101 DH5d (pCRW5-1; SEQ ID. NO: 47) | Accession No. NRRL B-21232 |
| 3. *E. coli* DH5d (pCRSTRIT1; SEQ ID NO: 1) | Accession No. NRRL B-21233 |
| 4. *E. coli* DH5d (pCRR1-21; SEQ ID NO: 4) | Accession No. NRRL B-21234 |
| 5. *E. coli* DH5d (pCRSNOD31; SEQ ID NO: 2) | Accession No. NRRL B-21235 |

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 548 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..548
        ( D ) OTHER INFORMATION: /note= "DNA sequence for the
            Internal Transcribed Spacer of Septoria tritici"

( x i ) SEQUENCE DESCRIPTION: SEQ ID NO:1:

```
TCCGTAGGTG AACCTGCGGA GGGATCATTA CCGAGCGAGG GCCTCCGGGT CCGACCTCCA      60
ACCCTTTGTG AACACATCCC GTTGCTTCGG GGGCGACCCT GCCGGGCGCC CCCGGAGGAC     120
CACCAAAAAA CACTGCATCT CTGCGTCGGA GTTTACGAGT AAATCGAAAC AAAACTTTCA     180
ACAACGGATC TCTTGGTTCT GGCATCGATG AAGAACGCAG CGAAATGCGA TAAGTAATGT     240
GAATTGCAGA ATTCAGTGAA TCATCGAATC TTTGAACGCA CATTGCGCCC CTGGTATTC      300
CGGGGGGCAT GCCCGTTCGA GCGTCATTAC ACCACTCCAG CCTCGCTGGG TATTGGGCGT     360
CTTTTCGCGG GGGATCACTC CCCCGCGCGC CTCAAAGTCT CCGGCTGAGC GGTCTCGTCT     420
CCCAGCGTTG TGGCATCACG TCTCGCCGCG GAGTTCACGA GCCCTCACGG CCGTTAAATC     480
```

|  |  |  |  |  |  |
|---|---|---|---|---|---|
| ACACCTCAGG | TTGACCTCGG | ATCGGGTAGG | GATACCCGCT | GAACTTAAGC | ATATCAATAA | 540
| GCGGAGGA |  |  |  |  |  | 548

( 2 ) INFORMATION FOR SEQ ID NO:2:

( i ) SEQUENCE CHARACTERISTICS:
        ( A ) LENGTH: 583 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Septoria nodorum ( i x ) FEATURE:
        ( A ) NAME/KEY: misc_feature
        ( B ) LOCATION: 1..583
  &nb

| | | | | | |
|---|---|---|---|---|---|
| GAAATCCTGG | GGGCTACCCT | ACTTGGTAGG | GTTTAGAGTC | GTCAGGCCGC | TCGGAGAAGC | 120 |
| CTGGTTCAGA | CCTCCACCCT | TGAATAAATT | ACCTTTGTTG | CTTTGGCAGG | GCGCCTCGCG | 180 |
| CCAGCGGCTT | CGGCTGTTGA | GTACCTGCCA | GAGGACCACA | ACTCTTGTTT | TTAGTGATGT | 240 |
| CTGAGTACTA | TATAATAGTT | AAAACTTTCA | ACAACGGATC | TCTTGGTTCT | GGCATCGATG | 300 |
| AAGAACGCAG | CGAAATGCGA | TAAGTAATGT | GAATTGCAGA | ATTCAGTGAA | TCATCGAATC | 360 |
| TTTGAACGCA | CATTGCGCCC | TCTGGTATTC | CGGGGGGCAT | GCCTGTTCGA | GCGTCATTAT | 420 |
| AACCACTCAA | GCTCTCGCTT | GGTATTGGGG | TTCGCGTCCT | CGCGGCCTCT | AAAATCAGTG | 480 |
| GCGGTGCCTG | TCGGCTCTAC | GCGTAGTAAT | ACTCCTCGCG | ATTGAGTCCG | GTAGGTTTAC | 540 |
| TTGCCAGTAA | CCCCCAATTT | TTTACAGGTT | GACCTCGGAT | CAGGTAGGGA | TACCCGCTGA | 600 |
| ACTTAAGCAT | ATCAATAAGC | GGAGGA | | | | 626 |

( 2 ) INFORMATION FOR SEQ ID NO:4:

( i ) SEQUENCE CHARACTERISTICS:
        ( A ) LENGTH: 627 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudocercosporella herpotrichoides
        ( B ) STRAIN: Strain R ( i x ) FEATURE:
        ( A ) NAME/KEY: misc_feature
        ( B ) LOCATION: 1..627
        ( D ) OTHER INFORMATION: /note= "DNA sequence for the
           Internal Transcribed Spacer of Pseudocercosporella
           herpotrichoides Strain R"

( x i ) SEQUENCE DESCRIPTION: SEQ ID NO:4:

| | | | | | |
|---|---|---|---|---|---|
| TCCGTAGGTG | AACCTGCGGA | AGGATCATTA | ATAGAGCAAT | GGATAGACAG | CGCCCCGGGA | 60 |
| GAAATCCTGG | GGGCCACCCT | ACTTCGGTAA | GGTTTAGAGT | CGTCGGGCCT | CTCGGAGAAG | 120 |
| CCTGGTCCAG | ACCTCCACCC | TTGAATAAAT | TACCTTTGTT | GCTTTGGCAG | GGCGCCTCGC | 180 |
| GCCAGCGGCT | TCGGCTGTTG | AGTACCTGCC | AGAGGACCAC | AACTCTTGTT | TTTAGTGATG | 240 |
| TCTGAGTACT | ATATAATAGT | TAAAACTTTC | AACAACGGAT | CTCTTGGTTC | TGGCATCGAT | 300 |
| GAAGAACGCA | GCGAAATGCG | ATAAGTAATG | TGAATTGCAG | AATTCAGTGA | ATCATCGAAT | 360 |
| CTTTGAACGC | ACATTGCGCC | CTCTGGTATT | CCGGGGGGCA | TGCCTGTTCG | AGCGTCATTA | 420 |
| TAACCACTCA | AGCTCTCGCT | TGGTATTGGG | GTTCGCGTCT | TCGCGGCCTC | TAAAATCAGT | 480 |
| GGCGGTGCCT | GTCGGCTCTA | CGCGTAGTAA | TACTCCTCGC | GATTGAGTCC | GGTAGGTTTA | 540 |
| CTTGCCAGCA | ACCCCCAATT | TTTTACAGGT | TGACCTCGGA | TCAGGTAGGG | ATACCCGCTG | 600 |
| AACTTAAGCA | TATCAATAAG | CGGAGGA | | | | 627 |

( 2 ) INFORMATION FOR SEQ ID NO:5:

( i ) SEQUENCE CHARACTERISTICS:
        ( A ) LENGTH: 534 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Mycosphaerella fijiensis ( i x ) FEATURE:
    ( A ) NAME/KEY: misc_feature
    ( B ) LOCATION: 1..534
    ( D ) OTHER INFORMATION: /note= "DNA sequence for the Internal Transcribed Spacer of Mycosphaerella fijiensis"

( x i ) SEQUENCE DESCRIPTION: SEQ ID NO:5:

```
TCCGTAGGTG  AACCTGCGGA  GGGATCATTA  CCGAGTGAGG  GCTCACGCCC  GACCTCCAAC    60
CCTTTGTGAA  CCACAACTTG  TTGCTTCGGG  GGCGACCTGC  CGTCGGCGGG  CGCCCCGGA    120
GGCCGTCTAA  ACACTGCATC  TTTGCGTCGG  AGTTTAAAAC  AAATCGAACA  AAACTTTCAA   180
CAACGGATCT  CTTGGTTCTG  GCATCGATGA  AGAACGCAGC  GAAATGCGAT  AAGTAATGTG   240
AATTGCAGAA  TTCAGTGAAT  CATCGAATCT  TGAACGCAC   ATTGCGCCCT  TTGGTATTCC   300
GAAGGGCATG  CCTGTTCGAG  CGTCATTTCA  CCACTCAAGC  CTGGCTTGGT  ATTGGGCGTC   360
GCGGTTCTTC  GCGCGCCTTA  AAGTCTCCGG  CTGAGCTGTC  CGTCTCTAAG  CGTTGTGGAT   420
CTTTCAATTC  GCTTCGGAGT  GCGGGTGGCC  GCGGCCGTTA  AATCTTTATT  CAAAGGTTGA   480
CCTCGGATCA  GGTAGGGATA  CCCGCTGAAC  TTAAGCATAT  CAATAAGCGG  AGGA         534
```

( 2 ) INFORMATION FOR SEQ ID NO:6:

( i ) SEQUENCE CHARACTERISTICS:
        ( A ) LENGTH: 540 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycosphaerella musicola ( i x ) FEATURE:
        ( A ) NAME/KEY: misc_feature
        ( B ) LOCATION: 1..540
        ( D ) OTHER INFORMATION: /note= "DNA sequence for the Internal Transcribed Spacer of Mycosphaerella musicola"

( x i ) SEQUENCE DESCRIPTION: SEQ ID NO:6:

```
TCCGTAGGTG  AACCTGCGGG  GGGATCATTA  CCGAGTGAGG  GCTCACCCCC  GACCTCCAAC    60
CCTTTGTGAA  CCACACCTGT  TGCTTCGGGG  GCGACCCTGC  CGGCGAACTT  GTCGCCGGGC   120
GCCCCCGGAG  GTCTCCTTAA  CACTGCATCT  CTGCGTCGGA  GTTCCAAACA  AATCGGACAA   180
AACTTTCAAC  AACGGATCTC  TTGGTTCTGG  CATCGATGAA  GAACGCAGCG  AAATGCGATA   240
AGTAATGTGA  ATTGCAGAAT  TCAGTGAATC  ATCGAATCTT  GAACGCACA   TTGCGCCTT    300
TGGCATTCCG  AAGGGCATGC  CTGTTCGAGC  GTCATTTCAC  CACTCAAGCC  TAGCTTGGTA   360
TTGGGCGCCG  CGGTGCTCCG  CGCGCCCAA   AGTCTCCGG   CTAAGCCGTC  CGTCTCTAAG   420
CGTTGTGGAT  TTTTCAGTTC  GCTCCGGAGC  GCGGGTGGCC  GCGGCCGTTA  AATCTTCAAA   480
GGTTGACCTC  GGATCAGGTA  GGGATACCCG  CTGAACTTAA  GCATATCAAT  AAGCGGAGGA   540
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB433

( i i i ) HYPOTHETICAL: NO ( i v ) ANTI-SENSE: NO ( x i ) SEQUENCE DESCRIPTION: SEQ ID NO:7:

ACACTCAGTA GTTTACTACT                                                          20

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB434

( i i i ) HYPOTHETICAL: NO ( i v ) ANTI-SENSE: NO ( x i ) SEQUENCE DESCRIPTION: SEQ ID NO:8:

TGTGCTGCGC TTCAATA                                                              17

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB525

( i i i ) HYPOTHETICAL: NO ( i v ) ANTI-SENSE: NO ( x i ) SEQUENCE DESCRIPTION: SEQ ID NO:9:

GCGACTTGTG CTGCGCTTCA ATA                                                   23

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB527

( i i i ) HYPOTHETICAL: NO ( i v ) ANTI-SENSE: NO ( x i ) SEQUENCE DESCRIPTION: SEQ ID NO:10:

CATTACACTC AGTAGTTTAC TACT                                                24

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB445

( i i i ) HYPOTHETICAL: NO ( i v ) ANTI-SENSE: NO ( x i ) SEQUENCE DESCRIPTION: SEQ ID NO:11:

CTGCGTCGGA GTTTACG 17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB446

( i i i ) HYPOTHETICAL: NO ( i v ) ANTI-SENSE: NO ( x i ) SEQUENCE DESCRIPTION: SEQ ID NO:12:

CGAGGCTGGA GTGGTGT 17

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB526

( i i i ) HYPOTHETICAL: NO ( i v ) ANTI-SENSE: NO ( x i ) SEQUENCE DESCRIPTION: SEQ ID NO:13:

CCCAGCGAGG CTGGAGTGGT GT 22

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB536

( i i i ) HYPOTHETICAL: NO ( i v ) ANTI-SENSE: NO ( x i ) SEQUENCE DESCRIPTION: SEQ ID NO:14:

CTGGGGGCTA CCCTACTTGG TAG 23

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB537

( i i i ) HYPOTHETICAL: NO ( i v ) ANTI-SENSE: NO ( x i ) SEQUENCE DESCRIPTION: SEQ ID NO:15:

GGGGGCTACC CTACTTGGTA G                     21

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB538

( i i i ) HYPOTHETICAL: NO ( i v ) ANTI-SENSE: NO ( x i ) SEQUENCE DESCRIPTION: SEQ ID NO:16:

ACTTGGTAGG GTTTAGAGTC GTCA                 24

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB539

( i i i ) HYPOTHETICAL: NO ( i v ) ANTI-SENSE: NO ( x i ) SEQUENCE DESCRIPTION: SEQ ID NO:17:

CTTCGGTAAG GTTTAGAGTC GTCG                 24

( 2 ) INFORMATION FOR SEQ ID NO:18:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB540

( i i i ) HYPOTHETICAL: NO ( i v ) ANTI-SENSE: NO ( x i ) SEQUENCE DESCRIPTION: SEQ ID NO:18:

GGGGGCCACC CTACTTCGGT AA                   22

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB541

( i i i ) HYPOTHETICAL: NO ( i v ) ANTI-SENSE: NO ( x i ) SEQUENCE DESCRIPTION: SEQ ID NO:19:

CCACTGATTT TAGAGGCCGC GAG                                                                                                     23

( 2 ) INFORMATION FOR SEQ ID NO:20:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB542

( i i i ) HYPOTHETICAL: NO ( i v ) ANTI-SENSE: NO ( x i ) SEQUENCE DESCRIPTION: SEQ ID NO:20:

CCACTGATTT TAGAGGCCGC GAA                                                                                                      23

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB543

( i i i ) HYPOTHETICAL: NO ( i v ) ANTI-SENSE: NO ( x i ) SEQUENCE DESCRIPTION: SEQ ID NO:21:

CCTGTAAAAA ATTGGGGGTT A                                                                                                         21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB544

( i i i ) HYPOTHETICAL: NO ( i v ) ANTI-SENSE: NO ( x i ) SEQUENCE DESCRIPTION: SEQ ID NO:22:

CCTGTAAAAA ATTGGGGGTT G                                                                                                         21

( 2 ) INFORMATION FOR SEQ ID NO:23:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB547

( i i i ) HYPOTHETICAL: NO ( i v ) ANTI-SENSE: NO ( x i ) SEQUENCE DESCRIPTION: SEQ ID NO:23:

ATTACCGAGT GAGGGCTCAC GC        22

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB548

( i i i ) HYPOTHETICAL: NO ( i v ) ANTI-SENSE: NO ( x i ) SEQUENCE DESCRIPTION: SEQ ID NO:24:

GTTGCTTCGG GGGCGACCTG        20

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB442

( i i i ) HYPOTHETICAL: NO ( i v ) ANTI-SENSE: NO ( x i ) SEQUENCE DESCRIPTION: SEQ ID NO:25:

TCGGGGGCGA CCTGCCG        17

( 2 ) INFORMATION FOR SEQ ID NO:26:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB443

( i i i ) HYPOTHETICAL: NO ( i v ) ANTI-SENSE: NO ( x i ) SEQUENCE DESCRIPTION: SEQ ID NO:26:

CCGGAGGCCG TCTA        14

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB545

( i i i ) HYPOTHETICAL: NO ( i v ) ANTI-SENSE: NO ( x i ) SEQUENCE DESCRIPTION: SEQ ID NO:27:

CCACAACGCT TAGAGACGGA CAG                        23

( 2 ) INFORMATION FOR SEQ ID NO:28:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB546

( i i i ) HYPOTHETICAL: NO ( i v ) ANTI-SENSE: NO ( x i ) SEQUENCE DESCRIPTION: SEQ ID NO:28:

CACCCGCACT CCGAAGCGAA TT                         22

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB549

( i i i ) HYPOTHETICAL: NO ( i v ) ANTI-SENSE: NO ( x i ) SEQUENCE DESCRIPTION: SEQ ID NO:29:

GATCCGAGGT CAACCTTTGA ATAA                      24

( 2 ) INFORMATION FOR SEQ ID NO:30:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB444

( i i i ) HYPOTHETICAL: NO ( i v ) ANTI-SENSE: NO ( x i ) SEQUENCE DESCRIPTION: SEQ ID NO:30:

GGTCAACCTT TGAATAA                              17

( 2 ) INFORMATION FOR SEQ ID NO:31:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Other nucleic acid
    ( A ) DESCRIPTION: Oligonucleotide primer JB451

( i i i ) HYPOTHETICAL: NO ( i v ) ANTI-SENSE: NO ( x i ) SEQUENCE DESCRIPTION: SEQ ID NO:31:

CCTTTGTGAA CCACACCT    18

( 2 ) INFORMATION FOR SEQ ID NO:32:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: Other nucleic acid
    ( A ) DESCRIPTION: Oligonucleotide primer JB440

( i i i ) HYPOTHETICAL: NO ( i v ) ANTI-SENSE: NO ( x i ) SEQUENCE DESCRIPTION: SEQ ID NO:32:

CTGCCGGCGA ACTT    14

( 2 ) INFORMATION FOR SEQ ID NO:33:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: Other nucleic acid
    ( A ) DESCRIPTION: Oligonucleotide primer JB449

( i i i ) HYPOTHETICAL: NO ( i v ) ANTI-SENSE: NO ( x i ) SEQUENCE DESCRIPTION: SEQ ID NO:33:

ACCCTGCCGG CGAACTT    17

( 2 ) INFORMATION FOR SEQ ID NO:34:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Other nucleic acid
    ( A ) DESCRIPTION: Oligonucleotide primer JB448

( i i i ) HYPOTHETICAL: NO ( i v ) ANTI-SENSE: NO ( x i ) SEQUENCE DESCRIPTION: SEQ ID NO:34:

GCGACCCTGC CGGCGAAC    18

( 2 ) INFORMATION FOR SEQ ID NO:35:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB441

( i i i ) HYPOTHETICAL: NO ( i v ) ANTI-SENSE: NO ( x i ) SEQUENCE DESCRIPTION: SEQ ID NO:35:

TAGCCGGGAG ACTTTGG                    17

( 2 ) INFORMATION FOR SEQ ID NO:36:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB450

( i i i ) HYPOTHETICAL: NO ( i v ) ANTI-SENSE: NO ( x i ) SEQUENCE DESCRIPTION: SEQ ID NO:36:

TCTGCGTCGG AGTTCC                     16

( 2 ) INFORMATION FOR SEQ ID NO:37:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer JB452

( i i i ) HYPOTHETICAL: NO ( i v ) ANTI-SENSE: NO ( x i ) SEQUENCE DESCRIPTION: SEQ ID NO:37:

CCGCGCTCCG GAGCGAAC                   18

( 2 ) INFORMATION FOR SEQ ID NO:38:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer ITS1

( i i i ) HYPOTHETICAL: NO ( i v ) ANTI-SENSE: NO ( x i ) SEQUENCE DESCRIPTION: SEQ ID NO:38:

TCCGTAGGTG AACCTGCGG                  19

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer ITS2

( i i i ) HYPOTHETICAL: NO ( i v ) ANTI-SENSE: NO ( x i ) SEQUENCE DESCRIPTION: SEQ ID NO:39:

GCTGCGTTCT TCATCGATGC     20

( 2 ) INFORMATION FOR SEQ ID NO:40:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer ITS3

( i i i ) HYPOTHETICAL: NO ( i v ) ANTI-SENSE: NO ( x i ) SEQUENCE DESCRIPTION: SEQ ID NO:40:

GCATCGATGA AGAACGCAGC     20

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer ITS4

( i i i ) HYPOTHETICAL: NO ( i v ) ANTI-SENSE: NO ( x i ) SEQUENCE DESCRIPTION: SEQ ID NO:41:

TCCTCCGCTT ATTGATATGC     20

( 2 ) INFORMATION FOR SEQ ID NO:42:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer OPB-12

( i i i ) HYPOTHETICAL: NO ( i v ) ANTI-SENSE: NO ( x i ) SEQUENCE DESCRIPTION: SEQ ID NO:42:

CCTTGACGCA     10

( 2 ) INFORMATION FOR SEQ ID NO:43:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer OPE-6

( i i i ) HYPOTHETICAL: NO ( i v ) ANTI-SENSE: NO ( x i ) SEQUENCE DESCRIPTION: SEQ ID NO:43:

AAGACCCCTC        10

( 2 ) INFORMATION FOR SEQ ID NO:44:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer OPE-12

( i i i ) HYPOTHETICAL: NO ( i v ) ANTI-SENSE: NO ( x i ) SEQUENCE DESCRIPTION: SEQ ID NO:44:

TTATCGCCCC        10

( 2 ) INFORMATION FOR SEQ ID NO:45:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer OPE-19

( i i i ) HYPOTHETICAL: NO ( i v ) ANTI-SENSE: NO ( x i ) SEQUENCE DESCRIPTION: SEQ ID NO:45:

ACCCCCGAAG        10

( 2 ) INFORMATION FOR SEQ ID NO:46:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide primer OPE-15

( i i i ) HYPOTHETICAL: NO ( i v ) ANTI-SENSE: NO ( x i ) SEQUENCE DESCRIPTION: SEQ ID NO:46:

ACGCACAACC        10

( 2 ) INFORMATION FOR SEQ ID NO:47:

( i ) SEQUENCE CHARACTERISTICS:
        ( A ) LENGTH: 627 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudocercosporella herpotrichoides
        ( B ) STRAIN: Strain W
        ( C ) INDIVIDUAL ISOLATE: Variant W5- 1

( i x ) FEATURE:
        ( A ) NAME/KEY: misc_feature
        ( B ) LOCATION: 1..627
        ( D ) OTHER INFORMATION: /note= "DNA sequence for the
            Internal Transcribed Spacer of Pseudocercosporella
            herpitrichoides strain W (variant W5-1)"

( x i ) SEQUENCE DESCRIPTION: SEQ ID NO:47:

```
TCCGTAGGTG  AACCTGCGGA  AGGATCATTA  ATAGAGCAAT  GAACAGACAG  CGCCCTGGGA       60
GAAATCCTGG  GGGCTACCCT  ACTTCGGTAG  GGTTTAGAGT  CGTCAGGCCT  CTCGGAGAAG      120
CCTGGTTCAG  ACCTCCACCC  TTGAATAAAT  TACCTTTGTT  GCTTTGGCAG  GGCGCCTCGC      180
GCCAGCGGCT  TCGGCTGTTG  AGTACCTGCC  AGAGGACCAC  AACTCTTGTT  TTTAGTGATG      240
TCTGAGTACT  ATATAATAGT  TAAAACTTTC  AACAACGGAT  CTCTTGGTTC  TGGCATCGAT      300
GAAGAACGCA  GCGAAATGCG  ATAAGTAATG  TGAATTGCAG  AATTCAGTGA  ATCATCGAAT      360
CTTTGAACGC  ACATTGCGCC  CTCTGGTATT  CCGGGGGGCA  TGCCTGTTCG  AGCGTCATTA      420
TAACCACTCA  AGCTCTCGCT  TGGTATTGGG  GTTCGCGTCC  TCGCGGCCTC  TAAAATCAGT      480
GGCGGTGCCT  CTCGGCTCTA  CGCGTAGTAA  TACTCCTCGC  GATTGAGTCC  GGTAGGTTTA      540
CTTGCCAGTA  ACCCCAATT   TTTTACAGGT  TGACCTCGGA  TCAGGTAGGG  ATACCCGCTG      600
AACTTAAGCA  TATCAATAAG  CGGAGGA                                             627
```

( 2 ) INFORMATION FOR SEQ ID NO:48:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: M13 universal -20 oligonucleotide primer ( i i i ) HYPOTHETICAL: NO ( i v ) ANTI-SENSE: NO ( x i ) SEQUENCE DESCRIPTION: SEQ ID NO:48:

```
GTAAAACGAC  GGCCAGT                                                          17
```

( 2 ) INFORMATION FOR SEQ ID NO:49:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other nucleic acid
( A ) DESCRIPTION: M13 universal reverse oligonucleotide primer ( i i i ) HYPOTHETICAL: NO ( i v ) ANTI-SENSE: NO ( x i ) SEQUENCE DESCRIPTION: SEQ ID NO:49:

A A C A G C T A T G   A C C A T G                                                                                                                                              1 6

What is claimed is:

1. An oligonucleotide primer for identification of a fungal pathogen, wherein said primer is selected from the group consisting of SEQ ID NOS: 7 to 37.

2. A pair of oligonucleotide primers for use in the amplification-based detection of a fungal Internal Transcribed Spacer Sequence, wherein at least one primer is selected from the group consisting of SEQ ID NOS: 7 to 37.

3. The pair of oligonucleotide primers according to claim 2, wherein one primer is selected from the group consisting of SEQ ID NOS: 7 to 37 and the other primer is selected from the group consisting of SEQ ID NOS: 38 to 41.

4. The pair of oligonucleotide primers according to claim 2, wherein said pair comprises SEQ ID NO: 7 and SEQ ID NO: 8.

5. The pair of oligonucleotide primers according to claim 2, wherein said pair comprises SEQ ID NO: 11 and SEQ ID NO: 9.

6. The pair of oligonucleotide primers according to claim 3, wherein said pair comprises SEQ ID NO: 12 and SEQ ID NO: 38.

7. The pair of oligonucleotide primers according to claim 3, wherein said pair comprises SEQ ID NO: 11 and SEQ ID NO: 41.

8. The pair of oligonucleotide primers according to claim 3, wherein said pair comprises SEQ ID NO: 29 and SEQ ID NO: 38.

9. The pair of oligonucleotide primers according to claim 3, wherein said pair comprises SEQ ID NO: 7 and SEQ ID NO: 41.

10. The pair of oligonucleotide primers according to claim 3, wherein said pair comprises SEQ ID NO: 30 and SEQ ID NO: 38.

11. An oligonucleotide primer for identification of a fungal pathogen, wherein said primer is selected from the group of primers consisting of SEQ ID NO: 42 to 46.

12. A method for the detection of a fungal pathogen, comprising the steps of:

(a) isolating DNA from a plant leaf infected with a pathogen;

(b) amplifying a part of the internal transcribed spacer sequence of said pathogen using said DNA as a template in a polymerase chain reaction with a pair of primers according to claims 2 or 3; and (c) detecting said fungal pathogen by visualizing said amplified part of the internal transcribed spacer sequence.

13. The method of claim 12, wherein said fungal pathogen is selected from S. nodorum, S. tritici, P. herpotrichoides, M. fijiensis, and M. musicola.

14. The method of claim 13, wherein said P. herpotrichoides is selected from strain W and strain R.

15. A method for the detection of a fungal pathogen, comprising the steps of:

(a) isolating DNA from a plant leaf infected with a pathogen;

(b) subjecting said DNA to polymerase chain reaction amplification using at least one primer according to claim 11; and (c) detecting said fungal pathogen by visualizing the product or products of said polymerase chain reaction amplification.

16. A kit comprising a carrier being compartmentalized to receive in close confinement therein one or more container means, one of said container means containing the primer of claim 1.

17. A kit comprising a carrier being compartmentalized to receive in close confinement therein one or more container means, one of said container means containing the primers of claim 4.

18. A kit comprising a carrier being compartmentalized to receive in close confinement therein one or more container means, one of said container means containing the primers of claim 5.

19. A kit comprising a carrier being compartmentalized to receive in close confinement therein one or more container means, one of said container means containing the primer of claim 11.

* * * * *